(12) United States Patent
Ashley

(10) Patent No.: US 8,658,189 B2
(45) Date of Patent: *Feb. 25, 2014

(54) METHODS OF TREATING ACNE

(71) Applicant: Galderma Laboratories, Inc., Fort Worth, TX (US)

(72) Inventor: Robert A. Ashley, Encinitas, CA (US)

(73) Assignee: Galderma Laboratories, Inc., Fort Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/838,559

(22) Filed: Mar. 15, 2013

(65) Prior Publication Data

US 2013/0203859 A1    Aug. 8, 2013

Related U.S. Application Data

(60) Continuation of application No. 13/277,789, filed on Oct. 20, 2011, which is a continuation of application No. 11/876,478, filed on Oct. 22, 2007, now Pat. No. 8,052,983, which is a continuation of application No. 10/757,656, filed on Jan. 14, 2004, now abandoned, which is a division of application No. 10/117,709, filed on Apr. 5, 2002, now Pat. No. 7,211,267.

(60) Provisional application No. 60/325,489, filed on Sep. 26, 2001, provisional application No. 60/281,916, filed on Apr. 5, 2001.

(51) Int. Cl.
*A61K 8/02* (2006.01)
*A61K 31/74* (2006.01)

(52) U.S. Cl.
USPC ........................................ 424/401; 424/78.05

(58) Field of Classification Search
None
See application file for complete search history.

(56) References Cited

U.S. PATENT DOCUMENTS 6,365,623 B1 * 4/2002 Perricone ...................... 514/448
6,455,583 B1 * 9/2002 Pflugfelder et al. .......... 514/528

* cited by examiner

*Primary Examiner* — Susan Tran
(74) *Attorney, Agent, or Firm* — Hoffmann & Baron, LLP

(57) ABSTRACT

A method of treating acne in a human in need thereof comprising administering systemically to said human a tetracycline compound in an amount that is effective to treat acne but has substantially no antibiotic activity, without administering a bisphosphonate compound.

20 Claims, 1 Drawing Sheet

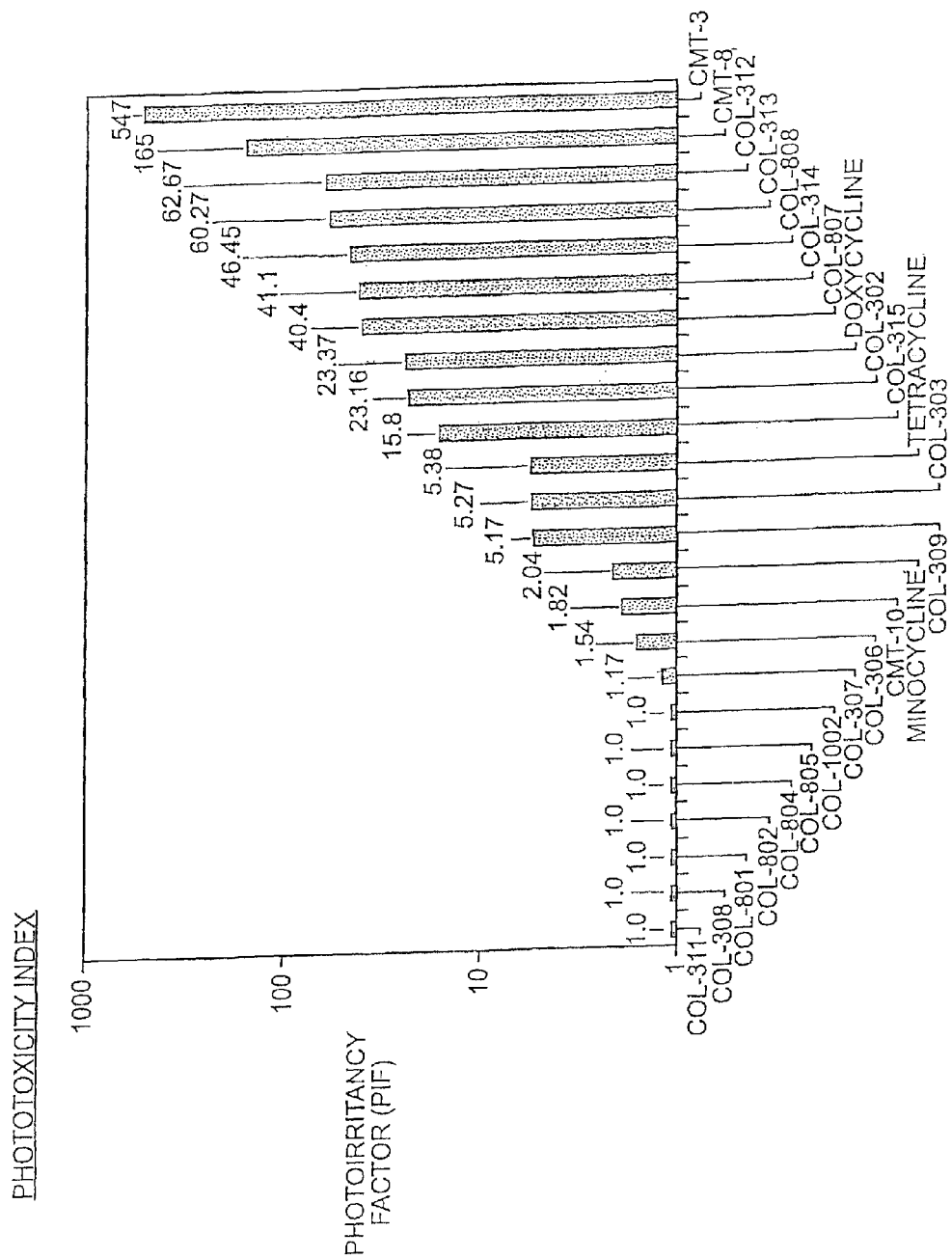

METHODS OF TREATING ACNE

CROSS-REFERENCE TO RELATED APPLICATION

This application is a continuation of U.S. application Ser. No. 13/277,789, filed on Oct. 20, 2011, pending, which is a continuation of U.S. application Ser. No. 11/876,478, filed on Oct. 22, 2007, now U.S. Pat. No. 8,052,983, which is a continuation of U.S. application Ser. No. 10/757,656, filed on Jan. 14, 2004, abandoned, which is a divisional application of U.S. application Ser. No. 10/117,709, filed on Apr. 5, 2002, now U.S. Pat. No. 7,211,267, which claims the benefit of U.S. Provisional Application No. 60/281,916, filed Apr. 5, 2001, and U.S. Provisional Application No. 60/325,489, filed Sep. 26, 2001. All of the aforementioned applications are incorporated herein by reference in their entireties.

BACKGROUND OF THE INVENTION

Acne is a common disease characterized by various types of lesions. The areas affected typically are areas of the skin where sebaceous glands are largest, most numerous, and most active. The lesions associated with acne are usually categorized as either non-inflammatory or inflammatory.

Non-inflammatory lesions include comedones. Comedones appear in two forms, open and closed. Comedones are thought to arise from abnormal follicular differentiation. Instead of undergoing shedding and discharge through the follicular orifice, abnormal desquamated cells (keratinocytes) become unusually cohesive, forming a microcomedo or a microscopic hyperkeratotic plug in the follicular canal. The progressive accumulation of these microcomedones lead to visible comedones.

In its mildest form, acne is a more or less superficial disorder characterized by slight, spotty skin irritations. In such cases, ordinary skin hygiene is typically a satisfactory treatment. In the more inflammatory types of acne, however, pustules; infected cysts; and in extreme cases, canalizing, inflamed and infected sacs appear. Without effective treatment, these lesions may become extensive and leave permanent, disfiguring scars.

Microorganisms, especially *Propionibacterium acnes*, are strongly implicated in the pathogenesis of acne. The microorganisms are thought to release microbial mediators of inflammation into the dermis or trigger the release of cytokines from ductal keratinocytes.

Accordingly, the efficacy of antibiotics in treating acne is thought to be due, in significant part, to the direct inhibitory effect of the antibiotics on the growth and metabolism of these microorganisms. Systemically-administered tetracycline antibiotics, especially minocycline hydrochloride, are particularly effective in treating acne.

The tetracyclines are a class of compounds of which tetracycline is the parent compound. Tetracycline has the following general structure:

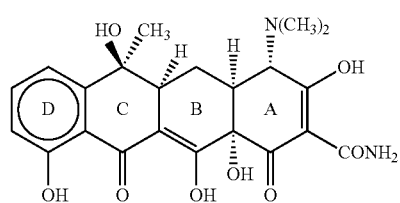

Structure A

The numbering system of the multiple ring nucleus is as follows:

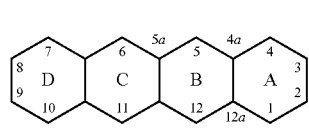

Structure B

Tetracycline, as well as the 5-hydroxy (oxytetracycline, e.g. Terramycin) and 7-chloro (chlorotetracycline, e.g. Aureomycin) derivatives, exist in nature, and are all well known antibiotics. Semisynthetic derivatives such as 7-dimethylaminotetracycline (minocycline) and 6α-deoxy-5-hydroxytetracycline (doxycycline) are also known tetracycline antibiotics. Natural tetracyclines may be modified without losing their antibiotic properties, although certain elements of the structure must be retained to do so.

In addition to the direct antibiotic activity of tetracyclines, further activities of antibiotic tetracyclines have been investigated for possible therapeutic effects on acne.

For example, a study by Elewski et al., *J. Amer. Acad. Dermatol.*, 8:807-812 (1983) suggests that acne therapy, consisting of orally-administered tetracycline at a total daily dose of 1000 mg, may have therapeutic anti-inflammatory effects in addition to antibiotic effects. In particular, it was found that the anti-inflammatory effect of tetracycline was, at least in part, due to inhibition of neutrophil chemotaxis induced by bacterial chemotactic factors.

A more recent study, performed by Eady et al., *J. Invest. Dermatol.*, 101:86-91 (1993), evaluated the effects of oral minocycline or tetracycline therapy on the cytokine and microflora content of open comedones in acne patients. The total daily dose of minocycline administered was 100 mg. The total daily dose of tetracycline administered was 1000 mg.

Eady et al. found that the therapies upregulated the production of bioactive IL-1α-like material and immunochemical IL-1β. IL-1 is considered to be a pro-inflammatory cytokine.

Accordingly to Eady et al., no overall decrease in the numbers of propionibacteria/mg of comedonal material was found. It is important to note, however, that the numbers of propionibacteria/mg of comedonal material are not expected to decrease in response to antibiotic therapy. Since the bacteria within comedones are encapsulated by the follicle, they are not susceptible to antibiotic treatment.

Another possible activity of tetracyclines in acne therapy was investigated by Bodokh, I., et al., *Acta. Derm. Venerol.*, 77:255-259 (1997). Their study was designed to evaluate the action of minocycline on sebaceous excretion in acne patients. A 100 mg daily dose of minocycline was administered. A subclinical increase in seborrhoea was reported. The authors propose that minocycline induces an increase in seborrhoea via a reduction in ductal obstruction. The mechanism by which the ductal obstruction is reduced is proposed to be a reduction in ductal irritation. The authors suggest that the reduction of ductal irritation is due to minocycline's direct effect on *P. acnes*, or minocycline's effect on the lipase produced by *P. acnes*.

Bodokh et al. also found that during treatment no correlation exists between seborrhoea intensity and clinical severity of acne. The authors state that the lack of correlation shows that seborrhoea is pathogenic because it is the "culture medium" of *P. acnes*. Thus, it can be concluded that the authors consider the antibiotic activity of minocycline to be therapeutically significant with respect to acne.

Similarly, in a recent clinical study it was reported that tetracycline in sub-antibiotic doses had no clinical effect on acne. (Cunliffe et al., *J. Am. Acad. Dermatol.*, 16:591-9 (1987).) In particular, a 100 mg total daily dose of minocycline and a 1.0 g total daily dose of tetracycline were found to be necessary to successfully treat acne.

The antibiotic effects of antibiotics are generally directly proportional to the dose administered of the antibiotics. Accordingly, in moderate to severe (i.e. inflammatory) forms of acne, oral antibiotics are typically administered at high doses. For example, in conventional acne therapy, tetracycline is administered at an initial dose of 500 to 2,000 mg/day, followed by a maintenance dose of 250-500 mg/day.

Clearly, the state-of-the-art teaching is that the clinical efficacy of systemically-administered tetracyclines in the treatment of acne is due, at least in significant part, to the antibiotic effects of the tetracyclines. In addition to their antibiotic effects, it has been proposed that tetracyclines reduce the number of inflammatory lesions (papules, pustules and nodules) by a variety of non-antibiotic mechanisms. Such mechanisms include interfering with the chemotaxis of polymorphonuclear leukocytes (PMN) into the inflammatory lesion, inhibition of PMN derived collagenase, and by scavenging reactive oxidative species produced by resident inflammatory cells.

There is no disclosure in the prior art of using either a sub-antibiotic dose of an antibiotic tetracycline compound, or of using a non-antibiotic tetracycline compound for the treatment of acne.

The use of tetracycline antibiotics, however, can lead to undesirable side effects. For example, the long term administration of antibiotic tetracyclines can reduce or eliminate healthy microbial flora, such as intestinal flora, and can lead to the production of antibiotic resistant organisms or the overgrowth of yeast and fungi.

Accordingly, there is a need for an effective treatment of acne which causes fewer undesirable side effects produced by the systemically-administered antibiotics used in conventional acne therapy.

SUMMARY OF INVENTION

The present invention provides a method of treating acne in a human in need thereof. The method comprises administering systemically to the human a tetracycline compound in an amount that is effective to treat acne but has substantially no antibiotic activity (i.e. substantially no antimicrobial activity), without administering a bisphosphonate compound.

Additionally, the present invention provides methods for reducing the number of comedones, inhibiting oxidation of melanin, and/or inhibiting lipid-associated abnormal follicular differentiation in a human in need thereof. These methods comprise administering systemically to the human a tetracycline compound in an amount that is effective for its purpose, e.g., to reduce the number of comedones, to inhibit oxidation of melanin, and/or to inhibit lipid-associated abnormal follicular differentiation, but has substantially no antibiotic activity.

BRIEF DESCRIPTION OF THE DRAWINGS

FIG. 1 shows the photoirritancy factor (PIF) for some tetracycline compounds. For structure K, the compounds indicated are as follows:

| COL | R7 | R8 | R9 |
|---|---|---|---|
| 308 | hydrogen | hydrogen | amino |
| 311 | hydrogen | hydrogen | palmitamide |
| 306 | hydrogen | hydrogen | dimethylamino |

For structures L, M, N or O the compounds indicated are as follows:

| COL | R7 | R8 | R9 |
|---|---|---|---|
| 801 | hydrogen | hydrogen | acetamido |
| 802 | hydrogen | hydrogen | dimethylaminoacetamido |
| 804 | hydrogen | hydrogen | nitro |
| 805 | hydrogen | hydrogen | amino |

For structure P, R8 is hydrogen and R9 is nitro.

DETAILED DESCRIPTION

The present invention provides methods of treating acne. As used herein, the term "acne" is a disorder of the skin characterized by papules, pustules, cysts, nodules, comedones, and other blemishes or skin lesions. These blemishes and lesions are often accompanied by inflammation of the skin glands and pilosebaceous follicles, as well as, microbial, especially bacterial, infection.

For the purposes of this specification, acne includes all known types of acne. Some types of acne include, for example, acne vulgaris, cystic acne, acne atrophica, bromide acne, chlorine acne, acne conglobata, acne cosmetica, acne detergicans, epidemic acne, acne estivalis, acne fulminans, halogen acne, acne indurata, iodide acne, acne keloid, acne mechanica, acne papulosa, pomade acne, premenstral acne, acne pustulosa, acne scorbutica, acne scrofulosorum, acne urticata, acne varioliformis, acne venenata, propionic acne, acne excoriee, gram negative acne, steroid acne, nodulocystic acne and acne rosacea. Acne rosacea is characterized by inflammatory lesions (erythema) and permanent dilation of blood vessels (telangectasia).

The present invention is particularly effective in treating comedones, e.g., reducing the number of comedones. Both open and closed comedones can be treated in accordance with the methods of this invention.

The present invention can also be used to treat certain other types of acneiform dermal disorders, e.g. perioral dermatitis, seborrheic dermatitis in the presence of acne, gram negative folliculitis, sebaceous gland dysfunction, hiddradenitis suppurativa, pseudo-folliculitis barbae, or folliculitis.

The method comprises the administration of a tetracycline compound to a human in an amount which is effective for its purpose e.g., the treatment of acne, including reducing the number of comedones, but which has substantially no antibiotic activity.

The tetracycline compound can be an antibiotic or non-antibiotic compound. The tetracycline compound has the general tetracycline structure indicated above, or a derivative thereof.

Some examples of antibiotic (i.e. antimicrobial) tetracycline compounds include doxycycline, minocycline, tetracycline, oxytetracycline, chlortetracycline, demeclocycline, lymecycline and their pharmaceutically acceptable salts. Doxycycline is preferably administered as its hyclate salt or as a hydrate, preferably monohydrate.

Non-antibiotic tetracycline compounds are structurally related to the antibiotic tetracyclines, but have had their antibiotic activity substantially or completely eliminated by chemical modification. For example, non-antibiotic tetracycline compounds are capable of achieving antibiotic activity comparable to that of tetracycline or doxycycline at concentrations at least about ten times, preferably at least about twenty five times, greater than that of tetracycline or doxycycline, respectively.

Examples of chemically modified non-antibiotic tetracyclines (CMTs) include 4-de(dimethylamino)tetracycline (CMT-1), tetracyclinonitrile (CMT-2), 6-demethyl-6-deoxy-4-de(dimethylamino)tetracycline (CMT-3), 7-chloro-4-de(dimethylamino)-tetracycline (CMT-4), tetracycline pyrazole (CMT-5), 4-hydroxy-4-de(dimethylamino)-tetracycline (CMT-6), 4-de(dimethylamino-12α-deoxytetracycline (CMT-7), 6-deoxy-5α-hydroxy-4-de(dimethylamino)tetracycline (CMT-8), 4-de(dimethylamino)-12α-deoxyanhydrotetracycline (CMT-9), 4-de(dimethylamino)minocycline (CMT-10).

Further examples of chemically modified non-antibiotic tetracyclines include Structures C-Z. (See Index of Structures.)

Tetracycline derivatives, for purposes of the invention, may be any tetracycline derivative, including those compounds disclosed generically or specifically in co-pending U.S. patent application Ser. No. 09/573,654 filed on May 18, 2000, which are herein incorporated by reference.

The minimal amount of the tetracycline compound administered to a human is the lowest amount capable of providing effective treatment of acne. Effective treatment is a reduction or inhibition of the blemishes and lesions associated with acne. The amount of the tetracycline compound is such that it does not significantly prevent the growth of microbes, e.g. bacteria.

Two ways in which to describe the administered amount of a tetracycline compound is by daily dose, and by serum level.

For example, tetracycline compounds that have significant antibiotic activity may be administered in a dose (i.e. amount) which is 10-80% of the antibiotic dose. More preferably, the antibiotic tetracycline compound is administered in a dose which is 40-70% of the antibiotic dose.

Some examples of antibiotic doses of members of the tetracycline family include 50, 75, and 100 mg/day of doxycycline; 50, 75, 100, and 200 mg/day of minocycline; 250 mg of tetracycline one, two, three, or four times a day; 1000 mg/day of oxytetracycline; 600 mg/day of demeclocycline; and 600 mg/day of lymecycline.

Examples of the maximum non-antibiotic doses of tetracyclines based on steady-state pharmacokinetics are as follows: 20 mg/twice a day for doxycycline; 38 mg of minocycline one, two, three or four times a day; and 60 mg of tetracycline one, two, three or four times a day.

In a preferred embodiment, to reduce the number of comedones, doxycycline is administered in a daily amount of from about 30 to about 60 milligrams, but maintains a concentration in human plasma below the threshold for a significant antibiotic effect.

In an especially preferred embodiment, doxycycline hyclate is administered at a 20 milligram dose twice daily. Such a formulation is sold for the treatment of periodontal disease by CollaGenex Pharmaceuticals, Inc. of Newtown, Pa. under the trademark Periostat®.

Example 38 below summarizes a clinical study using 20 mg doxycycline hyclate tablets administered twice a day. A significant reduction in the number of comedones was observed. This reduction in the number of comedones is unexpected. The reduction is particularly unexpected since, as can be seen from the microbiology results in Example 38, the treatment with doxycycline resulted in no reduction of skin microflora vis-à-vis a placebo control.

The administered amount of a tetracycline compound described by serum levels follows.

An antibiotic tetracycline compound is advantageously administered in an amount that results in a serum tetracycline concentration which is 10-80% of the minimum antibiotic serum concentration. The minimum antibiotic serum concentration is the lowest concentration known to exert a significant antibiotic effect.

Some examples of the approximate antibiotic serum concentrations of members of the tetracycline family follow.

For example, a single dose of two 100 mg minocycline HCl tablets administered to adult humans results in minocycline serum levels ranging from 0.74 to 4.45 µg/ml over a period of an hour. The average level is 2.24 µg/ml.

Two hundred and fifty milligrams of tetracycline HCl administered every six hours over a twenty-four hour period produces a peak plasma concentration of approximately 3 µg/ml. Five hundred milligrams of tetracycline HCl administered every six hours over a twenty-four hour period produces a serum concentration level of 4 to 5 µg/ml.

In one embodiment, the tetracycline compound can be administered in an amount which results in a serum concentration between about 0.1 and 10.0 µg/ml, more preferably between 0.3 and 5.0 µg/ml. For example, doxycycline is administered in an amount which results in a serum concentration between about 0.1 and 0.8 µg/ml, more preferably between 0.4 and 0.7 µg/ml.

Some examples of the plasma antibiotic threshold levels of tetracyclines based on steady-state pharmacokinetics are as follows: 1.0 µg/ml for doxycycline; 0.8 µg/ml for minocycline; and 0.5 µg/ml for tetracycline.

Non-antibiotic tetracycline compounds can be used in higher amounts than antibiotic tetracyclines, while avoiding the indiscriminate killing of microbes, and the emergence of resistant microbes. For example, 6-demethyl-6-deoxy-4-de(dimethylamino)tetracycline (CMT-3) may be administered in doses of about 40 to about 200 mg/day, or in amounts that result in serum levels of about 1.55 µg/ml to about 10 µg/ml.

The actual preferred amounts of tetracycline compounds in a specified case will vary according to the particular compositions formulated, the mode of application, the particular sites of application, and the subject being treated.

The tetracycline compounds can be in the form of pharmaceutically acceptable salts of the compounds. The term "pharmaceutically acceptable salt" refers to a salt prepared from tetracycline compounds and pharmaceutically acceptable non-toxic acids or bases. The acids may be inorganic or organic acids of tetracycline compounds. Examples of inorganic acids include hydrochloric, hydrobromic, hydroiodic, sulfuric, and phosphoric acids. Examples of organic acids include carboxylic and sulfonic acids. The radical of the organic acids may be aliphatic or aromatic. Some examples of organic acids include formic, acetic, phenylacetic, propionic, succinic, glycolic, glucuronic, maleic, furoic, glutamic, benzoic, anthranilic, salicylic, phenylacetic, mandelic, embonic (pamoic), methanesulfonic, ethanesulfonic, panthenoic, benzenesulfonic, stearic, sulfanilic, alginic, tartaric, citric, gluconic, gulonic, arylsulfonic, and galacturonic acids. Appropriate organic bases may be selected, for example, from N,N-dibenzylethylenediamine, chloroprocaine, choline, diethanolamine, ethylenediamine, meglumine (N-methylglucamine), and procaine.

The tetracycline compounds mentioned above, especially doxycycline and minocycline, are unexpectedly effective in reducing the number of comedones when administered at a dose which has substantially no antibiotic effect. Preferably the reduction is at least about 20% greater than for a placebo control, more preferably at least about 30% greater than for a placebo control, most preferably at least about 40% greater than for a placebo control, and optimally at least about 50% greater than for a placebo control.

The inventors are not certain of, and do not wish to be limited by, any particular mechanism of action. Nevertheless, it is believed that the ability of tetracyclines, such as doxycycline, to inhibit oxidation of melanin and to inhibit lipid-associated abnormal follicular differentiation prevents keratinocytes from becoming cohesive, thereby inhibiting the formation of comedones.

Preferably, the tetracycline compounds have low phototoxicity, or are administered in an amount that results in a serum level at which the phototoxicity is acceptable. Phototoxicity is a chemically-induced photosensitivity. Such photosensitivity renders skin susceptible to damage, e.g. sunburn, blisters, accelerated aging, erythemas and eczematoid lesions, upon exposure to light, in particular ultraviolet light. The preferred amount of the tetracycline compound produces no more phototoxicity than is produced by the administration of a 40 mg total daily dose of doxycycline.

Phototoxicity can be evaluated in terms of a photoirritancy factor (PIF), as described in the examples. A PIF value of about 1.0 indicates that a compound is considered to have no measurable phototoxicity.

The low phototoxic derivatives preferably have PIF values no greater than about 5, preferably no greater than about 2, more preferably no greater than about 1.5, most preferably no greater than about 1.2, and optimally about 1.

Some antibiotic tetracyclines having low phototoxicity include, for example, minocycline and tetracycline.

Some non-antibiotic tetracyclines having low phototoxicity include, but are not limited to, tetracycline compounds having the general formulae:

Structure K wherein: R7, R8, and R9 taken together in each case, have the following meanings:

| R7 | R8 | R9 |
|---|---|---|
| hydrogen | hydrogen | amino |
| hydrogen | hydrogen | palmitamide |
| hydrogen | hydrogen | dimethylamino | and

Structure L Structure M

Structure N Structure O wherein: R7, R8, and R9 taken together in each case, have the following meanings: and

| R7 | R8 | R9 |
|---|---|---|
| hydrogen | hydrogen | acetamido |
| hydrogen | hydrogen | dimethylaminoacetamido |

| R7 | R8 | R9 |
|---|---|---|
| hydrogen | hydrogen | nitro |
| hydrogen | hydrogen | amino |

Structure P wherein: R8, and R9 taken together are, respectively, hydrogen and nitro.

The tetracycline compounds are administered without administering a bisphosphonate compound. Bisphosphonates compounds are related to inorganic pyrophosphonic acid. The bisphosphonates include, as non-limiting examples, alendronate ((4-amino-1-hydroxybutylidene)bisphosphonic acid), clodronate (dichloromethane diphosphonic acid), etidronate ((1-hydroxyethylidene)diphosphanic acid) and pamidronate ((3-amino-1-hydroxypropylidene)bisphosphonic acid); also risedronate ([-hydroxy-2-(3-pyridinyl)ethylidene]bisphosphonic acid), tiludronate, i.e., tiludronic acid ([(4-chlorophenyl)thio]methylene]bisphosphonic acid) and zolendronate.

The tetracycline compounds may, for example, be administered systemically. For the purposes of this specification, "systemic administration" means administration to a human by a method that causes the compounds to be absorbed into the bloodstream.

For example, the tetracyclines compounds can be administered orally by any method known in the art. For example, oral administration can be by tablets, capsules, pills, troches, elixirs, suspensions, syrups, wafers, chewing gum and the like.

Additionally, the tetracycline compounds can be administered enterally or parenterally, e.g., intravenously; intramuscularly; subcutaneously, as injectable solutions or suspensions; intraperitoneally; or rectally. Administration can also be intranasally, in the form of, for example, an intranasal spray; or transdermally, in the form of, for example, a patch.

For the pharmaceutical purposes described above, the tetracycline compounds of the invention can be formulated per se in pharmaceutical preparations optionally with a suitable pharmaceutical carrier (vehicle) or excipient as understood by practitioners in the art. These preparations can be made according to conventional chemical methods.

In the case of tablets for oral use, carriers which are commonly used include lactose and corn starch, and lubricating agents such as magnesium stearate are commonly added. For oral administration in capsule form, useful carriers include lactose and corn starch. Further examples of carriers and excipients include milk, sugar, certain types of clay, gelatin, stearic acid or salts thereof, calcium stearate, talc, vegetable fats or oils, gums and glycols.

When aqueous suspensions are used for oral administration, emulsifying and/or suspending agents are commonly added. In addition, sweetening and/or flavoring agents may be added to the oral compositions.

For intramuscular, intraperitoneal, subcutaneous and intravenous use, sterile solutions of the tetracycline compounds can be employed, and the pH of the solutions can be suitably adjusted and buffered. For intravenous use, the total concentration of the solute(s) can be controlled in order to render the preparation isotonic.

The tetracycline compounds of the present invention can further comprise one or more pharmaceutically acceptable additional ingredient(s) such as alum, stabilizers, buffers, coloring agents, flavoring agents, and the like.

The tetracycline compound may be administered intermittently. For example, the tetracycline compound may be administered 1-6 times a day, preferably 1-4 times a day.

Alternatively, the tetracycline compound may be administered by sustained release. Sustained release administration is a method of drug delivery to achieve a certain level of the drug over a particular period of time. The level typically is measured by serum concentration. Further description of methods of delivering tetracycline compounds by sustained release can be found in the patent application, "Controlled Delivery of Tetracycline and Tetracycline Derivatives," filed on Apr. 5, 2001 and assigned to CollaGenex Pharmaceuticals, Inc. of Newtown, Pa. The aforementioned application is incorporated herein by reference in its entirety. For example, 40 milligrams of doxycycline may be administered by sustained release over a 24 hour period.

In the embodiment in which the tetracycline compound is a non-antibiotic tetracycline compound, administration can include topical application. Particular non-antibiotic tetracycline compounds have only limited biodistribution, e.g. CMT-5. In such cases, topical application is the preferred method of administration of the compound.

Carrier compositions deemed to be suited for topical use include gels, salves, lotions, creams, ointments and the like. The non-antibiotic tetracycline compound can also be incorporated with a support base or matrix or the like which can be directly applied to skin.

Topical application of non-antibiotic tetracycline compounds are effective in treating acne while not inducing significant toxicity in the human. For example, amounts of up to about 25% (w/w) in a vehicle are effective. Amounts of from about 0.1% to about 10% are preferred.

Combined or coordinated topical and systemic administration of the tetracycline compounds is also contemplated under the invention. For example, a non-absorbable non-antibiotic tetracycline compound can be administered topically, while a tetracycline compound capable of substantial absorption and effective systemic distribution in a human can be administered systemically.

The tetracycline compounds are prepared by methods known in the art. For example, natural tetracyclines may be modified without losing their antibiotic properties, although certain elements of the structure must be retained. The modifications that may and may not be made to the basic tetracycline structure have been reviewed by Mitscher in *The Chemistry of Tetracyclines*, Chapter 6, Marcel Dekker, Publishers, New York (1978). According to Mitscher, the substituents at positions 5-9 of the tetracycline ring system may be modified without the complete loss of antibiotic properties. Changes to the basic ring system or replacement of the substituents at positions 1-4 and 10-12, however, generally lead to synthetic tetracyclines with substantially less or effectively no antibiotic activity.

Further methods of preparing the tetracycline compounds are described in the examples.

EXAMPLES

The following examples serve to provide further appreciation of the invention but are not meant in any way to restrict the effective scope of the invention.

Preparation of Compounds

Example 1

4-Dedimethylamino-7-dimethylamino-6-demethyl-6-deoxy-9-nitrotetracycline sulfate To a solution of one millimole of 4-dedimethylamino-7-dimethylamino-6-demethyl-6-deoxytetracycline in 25 ml of concentrated sulfuric acid at 0° C. was added 1.05 mmole of potassium nitrate. The resulting solution was stirred at ice bath temperature for 15 minutes and poured in one liter of cold ether with stifling. The precipitated solid was allowed to settle and the majority of solvent decanted. The remaining material was filtered through a sintered glass funnel and the collected solid was washed well with cold ether. The product was dried in a vacuum desiccator overnight.

Example 2

9-amino-4-dedimethylamino-7-dimethylamino-6-demethyl-6-deoxytetracycline sulfate To a solution of 300 mg of the 9-nitro compound from example 1, in 30 ml of ethanol was added 50 mg of $PtO_2$. The mixture was hydrogenated at atmospheric pressure until the theoretical amount of hydrogen was absorbed. The system is flushed with nitrogen, the catalyst $PtO_2$ is filtered and the filtrate added dropwise to 300 ml of ether. The product that separates is filtered and dried in a vacuum desiccator.

Example 3

9-Acetamido-4-dedimethylamino-7-dimethylamino-6-demethyl-6-deoxytetracycline sulfate To a well stirred cold solution of 500 mg of 9-amino-4-dedimethylamino-7-dimethylamino-6-demethyl-6-deoxytetracycline sulfate from example 2, in 2.0 ml of 1,3-dimethyl-2-imidazolidinone, 500 mg of sodium bicarbonate was added followed by 0.21 ml of acetyl chloride. The mixture is stirred at room temperature for 30 minutes, filtered and the filtrate was added dropwise to 500 ml of ether. The product that separated was filtered and dried in a vacuum desiccator.

Example 4

4-Dedimethylamino-7-dimethylamino-6-demethyl-6-deoxy-9-diazoniumtetracycline sulfate To a solution of 0.5 g of 9-amino-4-dedimethylamino-7-dimethylamino-6-demethyl-6-deoxytetracycline sulfate, from example 2, in 10 ml of 0.1N hydrochloric acid in methanol cooled in an ice bath, 0.5 ml of n-butyl nitrite was added. The solution was stirred at ice bath temperature for 30 minutes and then poured into 250 ml of ether. The product that separated was filtered, washed with ether and dried in a vacuum desiccator.

Example 5

9-Azido-4-dedimethylamino-7-dimethylamino-6-demethyl-6-deoxytetracycline sulfate To a solution of 0.3 mmole of 4-dedimethylamino-7-dimethylamino-6-demethyl-6-deoxy-9-diazoniumtetracycline sulfate, from example 4, 10 ml of 0.1 N methanolic hydrogen chloride was added 0.33 mmole of sodium azide. The mixture was stirred at room temperature for 1.5 hours. The reaction mixture was then poured into 200 ml of ether. The product that separated was filtered and dried in a vacuum desiccator.

Example 6

9-Amino-8-chloro-4-dedimethylamino-7-dimethylamino-6-demethyl-6-deoxytetracycline sulfate One gram of 9-azido-4-dedimethylamino-7-dimethylamino-6-demethyl-6-deoxytetracycline hydrochloride, from example 4, was dissolved in 10 ml of concentrated sulfuric acid saturated with HCL at 0° C. The mixture was stirred at ice bath temperature for 1.5 hours and then slowly added dropwise to 500 ml of cold ether. The product that separated was filtered, washed with ether and dried in a vacuum desiccator.

Example 7

4-Dedimethylamino-7-dimethylamino-6-demethyl-6-deoxy-9-ethoxythiocarbonylthiotetracycline sulfate A solution of 1.0 mmole of 4-dedimethylamino-7-dimethylamino-6-demethyl-6-deoxy-9-diazoniumtetracycline sulfate, from example 4, in 15 ml of water was added to a solution of 1.15 mmole of potassium ethyl xanthate in 15 ml of water. The mixture was stirred at room temperature for one hour. The product separated and was filtered and dried in a vacuum desiccator.

Example 8A

General Procedure for Nitration

To 1 mmole of a 4-dedimethylamino-6-deoxytetracycline in 25 ml of concentrated sulfuric acid at 0° C. was added 1 mmole of potassium nitrate with stifling. The reaction solution was stirred for 15 minutes and then poured into 100 g of chopped ice. The aqueous solution was extracted 5 times with 20 ml of butanol each time. The butanol extracts were washed three times with 10 ml of water each time, and concentrated in vacuo to a volume of 25 ml. The light yellow crystalline solid which precipitated was filtered, washed with 2 ml of butanol and dried in vacuo at 60° C. for 2 hours. This solid was a mixture of the two mononitro isomers.

Example 8B

4-Dedimethylamino-6-deoxy-9-nitrotetracycline

To 980 mg of the nitration product from 4-dedimethylamino-6-deoxytetracycline (a mixture of the 2 isomers) in 25 ml of methanol was added enough triethylamine to dissolve the solid. The filtered solution (pH 9.0) was adjusted to pH 5.2 with concentrated sulfuric acid. A crystalline yellow solid (236 mg.) was obtained (29% yield). The material at this point was quite pure and contained only small amounts of the 7-isomer. Final purification was accomplished by liquid partition chromatography using a diatomaceous earth packed column and the solvent system: chloroform: butanol: 0.5 M phosphate buffer (pH 2) (16:1:10).

Example 9

4-Dedimethylamino-6-deoxy-7-nitrotetracycline

The methanol filtrate from example 8 was immediately adjusted to pH 1.0 with concentrated sulfuric acid. The light yellow crystalline solid, which was obtained as the sulfate salt. A purified free base was obtained by adjusting an aqueous solution of the sulfate salt (25 mg/ml) to pH 5.2 with 2 N sodium carbonate.

Example 10

9-Amino-4-dedimethylamino-6-deoxytetracycline

To a solution of 300 mg of the 9-nitro compound, prepared in example 8, in 30 ml of ethanol was added 50 mg of $PtO_2$. The mixture was hydrogenated at atmospheric pressure until the theoretical amount of hydrogen was absorbed. The system is flushed with nitrogen, the $PtO_2$ catalyst is filtered and the filtrate added dropwise to 300 ml of ether. The solid that separates is filtered and dried in a vacuum desiccator.

Example 11

9-Acetamido-4-dedimethylamino-6-deoxytetracycline sulfate

To well stirred cold solution of 500 mg of 9-amino-4-dedimethylamino-6-deoxytetracycline sulfate, from example 10, in 2.0 ml of 1,3-dimethyl-2-imidazolidinone was added 500 mg of sodium bicarbonate followed by 0.21 ml of acetyl chloride. The mixture was stirred at room temperature for 30 minutes, filtered and the filtrate was added dropwise to 500 ml of ether. The solid that separated was filtered and dried in a vacuum desiccator.

Example 12

4-Dedimethylamino-6-deoxy-9-diazoniumtetracycline sulfate

To a solution of 0.5 g of 9-amino-4-dedimethylamino-6-deoxytetracycline sulfate, from example 10, in 10 ml of 0.1N hydrochloric acid in methanol cooled in an ice bath was added 0.5 ml of n-butyl nitrite. The solution was stirred at ice bath temperature for 30 minutes and the poured into 250 ml of ether. The solid that separated was filtered, washed with ether and dried in a vacuum desiccator.

Example 13

9-Azido-4-dedimethylamino-6-deoxytetracycline sulfate

To a solution of 0.3 mmole of 4-dedimethylamino-6-deoxy-9-diazoniumtetracycline sulfate, of example 12, 10 ml of 0.1 N methanolic hydrogen chloride was added 0.33 mmole of sodium azide. The mixture was stirred at room temperature for 1.5 hours. The reaction mixture was then poured into 200 ml of ether. The solid that separated was filtered and dried in a vacuum desiccator.

Example 14

9-Amino-8-chloro-4-dedimethylamino-6-deoxytetracycline sulfate

One gram of 9-azido-4-dedimethylamino-7-dimethylamino-6-deoxytetracycline hydrochloride, from example 13, was dissolved in 10 ml of concentrated sulfuric acid saturated with HCL at 0° C. The mixture was stirred at ice bath temperature for 1.5 hours and then slowly added dropwise to 500 ml of cold ether. The solid that separated was filtered, washed and ether and dried in a vacuum desiccator.

Example 15

4-Dedimethylamino-6-deoxy-9-ethoxythiocarbon-ylthiotetracycline sulfate

A solution of 1.0 mmole of 4-dedimethylamino-6-deoxy-9-diazoniumtetracycline sulfate, from example 12, in 15 ml of water was added to a solution of 1.15 mmole of potassium ethyl xanthate in 15 ml of water. The mixture was stirred at room temperature for one hour. The solid that separated was filtered and dried in a vacuum desiccator.

Example 16

9-Dimethylamino-4-dedimethylamino-6-deoxytetra-cycline sulfate

To a solution of 100 mg. of the 9-amino compound from example 10, in 10 ml of ethylene glycol monomethyl ether is added 0.05 ml of concentrated sulfuric acid, 0.4 ml. of a 40% aqueous formaldehyde solution and 100 mg of a 10% palladium on carbon catalyst. The mixture is hydrogenated under atmospheric pressure and room temperature for 20 minutes. The catalyst was filtered and the filtrate was evaporated to dryness under reduced pressure. The residue is dissolved in 5 ml of methanol and this solution was added to 100 ml of ether. The product that separated was filtered and dried, yield, 98 mg.

Example 17

7-Amino-4-dedimethylamino-6-deoxytetracycline

This compound can be made using Procedure A or B. Procedure A. To a solution of 300 mg of the 7-nitro compound, from example 1, in 30 ml of ethanol was added 50 mg of $PtO_2$. The mixture was hydrogenated at atmospheric pressure until the theoretical amount of hydrogen was absorbed. The system is flushed with nitrogen, the catalyst $PtO_2$ is filtered and the filtrate added dropwise to 300 ml of ether. The solid that separates is filtered and dried in a vacuum desiccator.

Procedure B. 1 g of 6-deoxy-4-dedimethylamino-tetracycline was dissolved in 7.6 ml THF and 10.4 ml methanesulfonic acid at −10° C. After warming the mixture to 0° C. a solution of 0.86 g of dibenzyl azodicarboxylate was added and the mixture stirred for 2 hours at 0° C. to yield 7-[1,2-bis(carbobenzyloxy)hydrazino]-4-dedimethylamino-6-deoxytetracycline. A solution of 1 millimole of this material in 70 ml 2-methoxyethanol, and 300 mg 10% Pd—C was hydrogenated at room temperature to give 7-amino-6-deoxy-4-dedimethylaminotetracycline.

Example 18

7-Amino-6-deoxy-5-hydroxy-4-dedimethylaminotet-racycline 1 g of 6-deoxy-5-hydroxy-4-dedimethylaminotetracycline 3 was dissolved in 7.6 ml THF and 10.4 ml methanesulfonic acid at −10° C. After warming the mixture to 0° C. a solution of 0.86 g dibenzyl azodicarboxylate in 0.5 ml THF was added and the mixture stirred for 2 hours at 0° C. to yield 7-[1,2-bis(carbobenzyloxy)hydrazino]-4-dedimethylamino-6-deoxy-5-hydroxytetracycline. A solution of 1 millimole of this material in 70 ml 2-methoxyethanol, and 300 mg 10% Pd—C was hydrogenated at room temperature to give 7-amino-6-deoxy-5-hydroxytetracycline.

Example 19

7-Acetamido-4-dedimethylamino-6-deoxy-5-hydrox-ytetracycline sulfate

To well stirred cold solution of 500 mg of 7-amino-4-dedimethylamino-6-deoxy-5-hydroxytetracycline sulfate, from example 18, in 2.0 ml of 1,3-dimethyl-2-imidazolidinone was added 500 mg of sodium bicarbonate followed by 0.21 ml of acetyl chloride. The mixture was stirred at room temperature for 30 minutes, filtered and the filtrate was added dropwise to 500 ml of ether. The solid that separated was filtered and dried in a vacuum desiccator.

Example 20

4-Dedimethylamino-6-deoxy-5-hydroxy-7-diazoni-umtetracycline hydrochloride

To a solution of 0.5 g of 7-amino-4-dedimethylamino-6-deoxy-5-hydroxytetracycline sulfate, from example 20, in 10 ml of 0.1N hydrochloric acid in methanol cooled in an ice bath was added 0.5 ml of n-butyl nitrite. The solution was stirred at ice bath temperature for 30 minutes and then poured into 250 ml of ether. The solid that separated was filtered, washed with ether and dried in a vacuum desiccator.

Example 21

7-Azido-4-dedimethylamino-6-deoxy-5-hydroxytet-racycline

To a solution of 0.3 mmole of 4-dedimethylamino-6-deoxy-5-hydroxy-7-diazoniumtetracycline hydrochloride, from example 20, 10 ml of 0.1 N methanolic hydrogen chloride was added 0.33 mmole of sodium azide. The mixture was stirred at room temperature for 1.5 hours. The reaction mixture was then poured into 200 ml of ether. The solid that separated was filtered and dried in a vacuum desiccator.

Example 22

7-Amino-8-chloro-4-dedimethylamino-6-deoxy-5-hydroxytetracycline sulfate

One gram of 7-azido-4-dedimethylamino-7-dimethy-lamino-6-deoxy-5-hydroxytetracycline sulfate, from example 21, was dissolved in 10 ml of concentrated sulfuric acid (previously saturated with hydrogen chloride) at 0° C. The mixture was stirred at ice bath temperature for 1.5 hours and then slowly added dropwise to 500 ml of cold ether. The solid that separated was filtered, washed with ether and dried in a vacuum desiccator.

Example 23

4-Dedimethylamino-6-deoxy-5-hydroxy-7-ethox-ythiocarbonylthiotetracycline

A solution of 1.0 mmole of 4-dedimethylamino-6-deoxy-5-hydroxy-7-diazoniumtetracycline hydrochloride, from example 20, in 15 ml of water was added to a solution of 1.15 mmole of potassium ethyl xanthate in 15 ml of water. The mixture was stirred at room temperature for one hour. The solid that separated was filtered and dried in a vacuum desiccator.

Example 24

7-Dimethylamino-4-dedimethylamino-6-deoxy-5-hydroxytetracycline sulfate

To a solution of 100 mg of the 7-amino compound in 10 ml of ethylene glycol monomethyl ether is added 0.05 ml of concentrated sulfuric acid, 0.4 ml of a 40% aqueous formaldehyde solution and 100 mg of a 10% palladium on carbon catalyst. The mixture is reduced with hydrogen at atmospheric pressure and room temperature for 20 minutes. The catalyst was filtered and the filtrate was evaporated to dryness under reduced pressure. The residue is dissolved in 5 ml of methanol and this solution was added to 100 ml of ether. The product that separated was filtered and dried, yield, 78 mg.

Example 25

7-Diethylamino-4-dedimethylamino-5-hydroxytetracycline sulfate

To a solution of 100 mg of the 7-amino compound in 10 ml of ethylene glycol monomethyl ether is added 0.05 ml of concentrated sulfuric acid, 0.4 ml of acetaldehyde and 100 mg of a 10% palladium on carbon catalyst. The mixture is reduced with hydrogen at atmospheric pressure at room temperature for 20 minutes. The catalyst was filtered and filtrate was evaporated to dryness under reduced pressure. The residue is dissolved in 5 ml of methanol and this solution was added to 100 ml of ether. The product that separated was filtered and dried.

Example 26

4-Dedimethylamino-6-deoxy-7-diazoniumtetracycline hydrochloride

To a solution of 0.5 g. of 7-amino-4-dedimethylamino-6-deoxytetracycline sulfate, from example 17, in 10 ml of 0.1N hydrochloric acid in methanol cooled in an ice bath was added 0.5 ml of n-butyl nitrite. The solution was stirred at ice bath temperature for 30 minutes and then poured into 250 ml of ether. The solid that separated was filtered, washed with ether and dried in a vacuum desiccator.

Example 27

7-Azido-4-dedimethylamino-6-deoxytetracycline

To a solution of 0.3 mmole of 4-dedimethylamino-6-deoxy-7-diazoniumtetracycline hydrochloride, from example 26, 10 ml of 0.1 N methanolic hydrogen chloride was added 0.33 mmole of sodium azide. The mixture was stirred at room temperature for 1.5 hours. The reaction mixture was then poured into 200 ml of ether. The solid that separated was filtered and dried in a vacuum desiccator.

Example 28

7-Amino-8-chloro-4-dedimethylamino-6-deoxytetracycline sulfate

One gram of 7-azido-4-dedimethylamino-7-dimethylamino-6-deoxytetracycline sulfate was dissolved in 10 ml of concentrated sulfuric acid (previously saturated with hydrogen chloride) at 0° C. The mixture was stirred at ice bath temperature for 1.5 hours and then slowly added dropwise to 500 ml of cold ether. The solid that separated was filtered, washed with ether and dried in a vacuum desiccator.

Example 29

4-Dedimethylamino-6-deoxy-7-ethoxythiocarbonylthiotetracycline

A solution of 1.0 mmole of 4-dedimethylamino-6-deoxy-7-diazoniumtetracycline hydrochloride, from example 26, in 15 ml of water was added to a solution of 1.15 mmole of potassium ethyl xanthate in 15 ml of water. The mixture was stirred at room temperature for one hour. The solid that separated was filtered and dried in a vacuum desiccator.

Example 30

7-Dimethylamino-4-dedimethylamino-6-deoxytetracycline sulfate

To a solution of 100 mg of the 7-amino compound, from example 26, in 10 ml of ethylene glycol monomethyl ether is added 0.05 ml of concentrated sulfuric acid, 0.4 ml of a 40% aqueous formaldehyde solution and 100 mg of a 10% palladium on carbon catalyst. The mixture is reduced with hydrogen at atmospheric pressure and room temperature for 20 minutes. The catalyst was filtered and the filtrate was evaporated to dryness under reduced pressure. The residue is dissolved in 5 ml of methanol and this solution was added to 100 ml of ether. The product that separated was filtered and dried.

Example 31

9-Acetamido-8-chloro-4-dedimethylamino-7-dimethylamino-6-deoxy-6-demethyltetracycline To well stirred cold solution of 500 mg of 9-amino-8-chloro-4-dedimethylamino-6-deoxy-6-demethyl-7-dimethyl amino tetracycline sulfate, from example 6, in 2.0 ml of 1,3-dimethyl-2-imidazolidinone was added 500 mg of sodium bicarbonate followed by 0.21 ml. of acetyl chloride. The mixture was stirred at room temperature for 30 minutes, filtered and the filtrate was added dropwise to 500 ml of ether. The solid that separated was filtered and dried in a vacuum desiccator.

Example 32

8-Chloro-4-dedimethylamino-7-dimethylamino-6-deoxy-6-demethyl-9-ethoxythiocarbonylthiotetracycline A solution of 1.0 mmole of -8-chloro-4-dedimethylamino-6-deoxy-6-demethyl-7-dimethyl amino-9-diazoniumtetracycline hydrochloride in 15 ml of water was added to a solution of 1.15 mmole of potassium ethyl xanthate in 15 ml of water. The mixture was stirred at room temperature for one hour. The solid that separated was filtered and dried in a vacuum desiccator.

Example 33

8-Chloro-9-dimethylamino-4-dedimethylamino-7-dimethylamino-6-deoxy-6-demethyletracycline sulfate

To a solution of 100 mg. of the 9-amino compound, from example 6, in 10 ml of ethylene glycol monomethyl ether is added 0.05 ml of concentrated sulfuric acid, 0.4 ml of acetaldehyde and 100 mg of a 10% palladium on carbon catalyst. The mixture is reduced with hydrogen at atmospheric pressure and room temperature for 20 minutes. The catalyst was filtered and the filtrate was evaporated to dryness under reduced pressure. The residue is dissolved in 5 ml of methanol and this solution was added to 100 ml of ether. The product that separated was filtered and dried.

Example 34

N-(4-methylpiperazin-1-yl)methyl-4-dedimethylamino-6-demethyl-6-deoxytetracycline

An aqueous solution of 58 mg (37%) formaldehyde (0.72 mmol) was added to a solution of 203 mg (0.49 mmol) of 4-dedimethylamino-6-demethyl-6-deoxytetracycline in 5.0 ml ethylene glycol dimethyl ether. The mixture was stirred at room temperature for 0.5 hours. 56 mg (0.56 mmol) of 1-methylpiperazine was then added and the resulting mixture was stirred overnight and refluxed for 20 minutes. The mixture was then cooled and a solid product was collected by filtration. The solid product was then washed with the solvent and dried by vacuum filtration.

Example 35

N-(4-methylpiperazin-1-yl)methyl-4-dedimethylamino-6-demethyl-6-deoxy-9-hexanoylaminotetracycline

An aqueous solution of 49 mg 37% formaldehyde (0.60 mmol) was added to a solution of 146 mg (0.30 mmol) of 4-dedimethylamino-6-demethyl-6-deoxy-9-hexanoylaminotetracycline in 5.0 ml ethylene glycol dimethyl ether. The mixture was stirred at room temperature for 0.5 hours. 60 mg (0.60 mmol) of 1-methylpiperazine was then added and the resulting mixture was stirred overnight and refluxed for 20 minutes. The mixture was then cooled and a solid product was collected by filtration. The solid product was then washed with the solvent and dried by vacuum filtration.

Example 36

4-Dedimethylamino-6-demethyl-6-deoxy-9-hexanoylaminotetracycline

1.54 g (7.2 mmol) of hexanoic anhydride and 150 mg of 10% Pd/C catalyst were added to 300 mg (0.72 mmol) of 4-dedimethylamino-6-demethyl-6-deoxytetracycline in 6.0 ml of 1,4-dioxane and 6.0 ml of methanol. The mixture was hydrogenated overnight at room temperature. The catalyst was removed by filtration and the filtrate was concentrated under reduced pressure. The residue was dissolved in 7 ml of ethyl acetate and triturated with 50 ml of hexane to produce a solid product. The solid product was filtered and dried by vacuum filtration.

Example 37

Phototoxicity Determination

BALB/c 3T3 (CCL-163) cells were obtained from ATCC and cultured in antibiotic-free Dulbecco's Minimum Essential Medium (4.5 g/l glucose)(DMEM) supplemented with L-glutamine (4 mM) and 10% newborn calf serum. The working cell bank was prepared and found to be free of mycoplasma. Streptomycin sulfate (100 µg/ml) and penicillin (100 IU/ml) were added to the medium after the cells were treated with test article in 96-well plates.

Serial dilutions of the tetracycline derivatives were prepared in DMSO at concentrations 100× to final testing concentration. The CMT dilutions in DMSO were then diluted in Hanks' Balanced Salt Solution (HBSS) for application to the cells. The final DMSO concentration was 1% in treated and control cultures. For the dose range finding assay, 8 serial dilutions covered a range of 100 to 0.03 mg/ml in half log steps while the definitive assays used 6 to 8 doses prepared in quarter log steps, centered on the expected 50% toxicity point. In many cases, the dose range for treatment without UV light was different from the dose range selected with UV light. One hundred µg/ml is the highest dose recommended to prevent false negative results from UV absorption by the dosing solutions.

Controls: Each assay included both negative (solvent) and positive controls. Twelve wells of negative control cultures were used on each 96-well plate. Chlorpromazine (Sigma) was used as the positive control and was prepared and dosed like the test tetracycline derivatives.

Solar Simulator: A Dermalight SOL 3 solar simulator, equipped with a UVA H1 filter (320-400 nm), was adjusted to the appropriate height. Measurement of energy through the lid of a 96-well microtiter plate was carried out using a calibrated UV radiometer UVA sensor. Simulator height was adjusted to deliver 1.7±0.1 m/Wcm$^2$ of UVA energy (resulting dose was 1 J/cm$^2$ per 10 min.)

Phototoxicity Assay: Duplicate plates were prepared for each test material by seeding 10$^4$ 3T3 cells per well in µl of complete medium 24 hours before treatment. Prior to treatment, the medium was removed, and the cells washed once with 125 µl prewarmed HBSS. Fifty µl of prewarmed HBSS were added to each well. Fifty µl of test article dilutions were added to the appropriate wells and the plates returned to the incubator for approximately one hour. Following the 1 hr incubation, the plates designated for the photoirritation assay were exposed (with the lid on) to 1.7±0.1 mW/cm$^2$ UVA light for 50±2 minutes at room temperature resulting in an irradiation dose of 5 J/cm2. Duplicate plates designated for the cytotoxicity assay were kept in the dark room temperature for 50±2 minutes. After the 50 minute exposure period the test article dilutions were decanted from the plates and the cells washed once with 125 µl HBSS. One hundred µl of medium were added to all wells and the cells incubated as above for 24±1 hours.

After 24 hours of incubation, the medium was decanted and 100 µl of the Neutral Red containing media added to each well. The plates were returned to the incubator and incubated for approximately 3 hours. After 3 hours, the medium was decanted and each well rinsed once with 250 µl of HBSS. The plates were blotted to remove the HBSS and 100 µl of Neutral Red Solvent were added to each well. After a minimum of 20 minutes of incubation at room temperature (with shaking), the absorbance at 550 nm was measured with a plate reader, using the mean of the blank outer wells as the reference. Relative survival was obtained by comparing the amount of neutral red taken by test article and positive control treated groups to the neutral red taken up by the negative group on the same plate. $IC_{50}$ values for both the UVA exposed and non-exposed groups were determined whenever possible. One dose range finding and at least two definitive trails were performed on each tetracycline derivative and control compound.

Determination of Phototoxicity: Phototoxicity of the tetracycline derivatives can be measured by its photoirritancy factor (PIF). The PIF was determined by comparing the $IC_{50}$ without UVA $[IC_{50}(-UVA)]$ with the $IC_{50}$ with UVA $[IC_{50}(+UVA)]$:

$$PIF = \frac{IC_{50}(-UVA)}{IC_{50}(+UVA)}$$

If both $IC_{50}$ values can be determined, the cut off value of the factor to discriminate between phototoxicants and non-phototoxicants is a factor of 5. A factor greater than 5 is indicative of phototoxic potential of the test material.

If $IC_{50}$ (+UVA) can be determined but $IC_{50}$(-UVA) cannot, the PIF cannot be calculated, although the compound tested may have some level of phototoxic potential. In this case, a ">PIF" can be calculated and the highest testable dose (-UVA) will be used for calculation of the ">PIF."

$$> PIF = \frac{\text{maximum dose }(-UVA)}{IC_{50}(+UVA)}$$

If both, $IC_{50}$(-UVA) and $IC_{50}$(+UVA) cannot be calculated because the chemical does not show cytotoxicty (50% reduction in viability) up to the highest dose tested, this would indicate a lack of phototoxic potential.

Example 38

Effects of Doxycycline Hyclate 20 mg (Dermastat) Tablets Administered Twice Daily for the Treatment of Moderate Acne Study Design:
  Multi-center, randomized double-blind, placebo-controlled;
  Sixty patients enrolled (30 doxycycline and 30 placebo);
  Six month duration of the study.
  Patients received medication twice daily, approximately 12 hours apart (placebo and drug are identical in appearance.)
Inclusion Criteria:
  Healthy post-pubescent males and females (age≥18) with moderate facial acne:
    Comedones 6 to 200;
    Inflammatory lesions 10 to 75 (papules and pustules, less than or equal to 5 nodules);
  Females tested negative for pregnancy and were non-lactating;
  Females maintained appropriate birth control;
  Patients signed an Informed Consent Form;
  No Accutane treatment for 6 months prior to baseline.
Exclusion Criteria:
  Use of hormonal contraception 6 months prior to baseline or during study;
  Use of topical acne treatments within 6 weeks of baseline or during study;
  Use of systemic antibiotics within 6 weeks of baseline or during study;
  Use of investigational drugs within 90 days of baseline;
  Use of any acne treatments during study.
Study Procedure:
  Patients reported to clinician at baseline and months 2, 4, and 6;
  Acne counts were taken at baseline and months 2, 4, and 6;
  Patient self-assessment and clinician's assessment (baseline, 2, 4, and 6);
  Facial photographs at baseline and months 2, 4, and 6;
  Drug dispensation at baseline and months 2 and 4;
  Adverse event recording at baseline and months 2, 4, and 6;
  Microbiological sampling at baseline and month 6;
  Clinical Labs at baseline and month 6.
Evaluations:
Efficacy:
  Change in lesion count of papules and pustules
  Change in comedone count
  Change in total lesion count (comedones and inflammatory lesions)
Microbiology:
  Reduction in skin flora between groups
  Increase in resistant counts between groups
Efficacy Results A six-month treatment with Dermastat resulted in: i) a 53.6% reduction in comedones vis-à-vis a 10.6% reduction of comedones in placebo (p<0.05); ii) a 50.1% reduction in inflammatory lesions vis-à-vis a 30.2% reduction of inflammatory lesions in placebo (p<0.01); and iii) a 52.3% reduction in total lesion count vis-à-vis a 17.5% reduction of inflammatory lesions in placebo (p<0.05).

Microbiology Results:

A six-month treatment with Dermastat resulted in no reduction of skin microflora (including *Propionibacterium acnes*) nor an increase in resistance counts when compared with placebo.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

Index of Structures

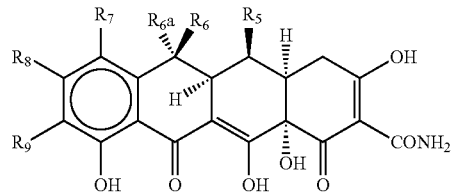

Structure C

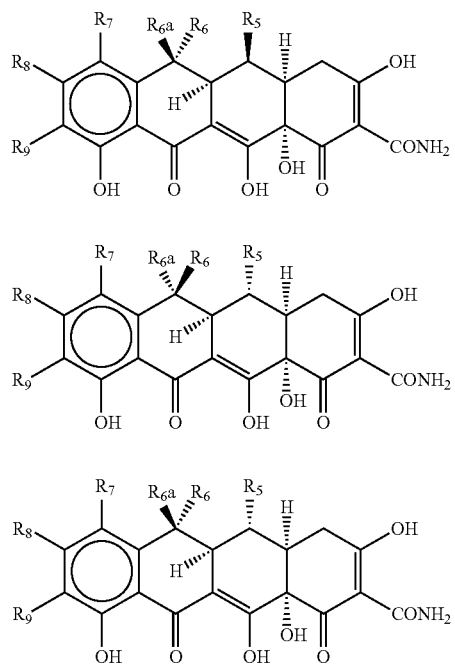

Structure D

Structure E

Structure F wherein R7 is selected from the group consisting of hydrogen, amino, nitro, mono(lower alkyl)amino, halogen, di(lower alkyl)amino, ethoxythiocarbonylthio, azido, acylamino, diazonium, cyano, and hydroxyl; R6-a is selected from the group consisting of hydrogen and methyl; R6 and R5 are selected from the group consisting of hydrogen and hydroxyl; R8 is selected from the group consisting of hydrogen and halogen; R9 is selected from the group consisting of hydrogen, amino, azido, nitro, acylamino, hydroxy, ethoxythiocarbonylthio, mono(lower alkyl)amino, halogen, diazonium, di(lower alkyl)amino and RCH(NH$_2$)CO; R is hydrogen or lower alkyl; and pharmaceutically acceptable and unacceptable salts thereof; with the following provisos: when either R7 and R9 are hydrogen then R8 must be halogen; and when R6-a, R6, R5 and R9 are all hydrogen and R7 is hydrogen, amino, nitro, halogen, dimethylamino or diethylamino, then R8 must be halogen; and when R6-a is methyl, R6 and R9 are both hydrogen, R5 is hydroxyl and R7 is hydrogen, amino, nitro, halogen or diethylamino, then R8 is halogen; and when R6-a is methyl, R6 is hydroxyl, R5, R7 and R9 are all hydrogen, then R8 must be halogen; and when R6-a, R6 and R5 are all hydrogen, R9 is methylamino and R7 is dimethylamino, then R8 must be halogen; and when R6-a is methyl, R6 is hydrogen, R5 is hydroxyl, R9 is methylamino and R7 is dimethylamino, then R8 must be halogen; and when R6-a is methyl, R6, R5 and R9 are all hydrogen and R7 is cyano, then R8 must be halogen.

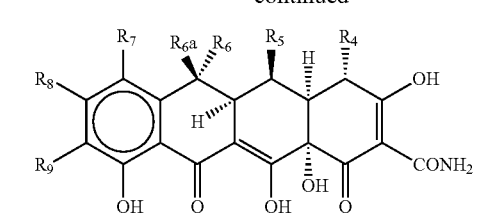

Structure H

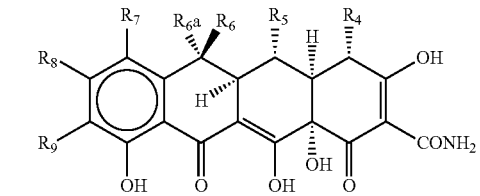

Structure I

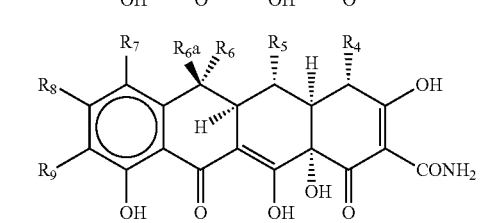

Structure J wherein R7 is selected from the group consisting of hydrogen, amino, nitro, mono(lower alkyl)amino, halogen, di(lower alkyl)amino, ethoxythiocarbonylthio, azido, acylamino, diazonium, cyano, and hydroxyl; R6-a is selected from the group consisting of hydrogen and methyl; R6 and R5 are selected from the group consisting of hydrogen and hydroxyl; R4 is selected from the group consisting of NOH, N—NH-A, and NH-A, where A is a lower alkyl group; R8 is selected from the group consisting of hydrogen and halogen; R9 is selected from the group consisting of hydrogen, amino, azido, nitro, acylamino, hydroxy, ethoxythiocarbonylthio, mono(lower alkyl)amino, halogen, di(lower alkyl)amino and RCH(NH$_2$)CO; R is hydrogen or lower alkyl; and pharmaceutically acceptable and unacceptable salts thereof; with the following provisos: when R4 is NOH, N—NH-alkyl or NH-alkyl and R7, R6-a, R6, R5, and R9 are all hydrogen, then R8 must be halogen; and when R4 is NOH, R6-a is methyl, R6 is hydrogen or hydroxyl, R7 is halogen, R5 and R9 are both hydrogen, then R8 must be halogen; and when R4 is N—NH-alkyl, R6-a is methyl, R6 is hydroxyl and R7, R5, R9 are all hydrogen, then R8 must be halogen; and when R4 is NH-alkyl, R6-a, R6, R5 and R9 are all hydrogen, R7 is hydrogen, amino, mono(lower alkyl)amino, halogen, di(lower alkyl) amino or hydroxyl, then R8 must be halogen; and when R4 is NH-alkyl, R6-a is methyl, R6 and R9 are both hydrogen, R5 is hydroxyl, and R7 is mono(lower alkyl)amino or di(lower alkyl)amino, then R8 must be halogen; and when R4 is NH-alkyl, R6-a is methyl, R6 is hydroxy or hydrogen and R7, R5, and R9 are all be hydrogen, then R8 must be halogen.

General Formula (I)

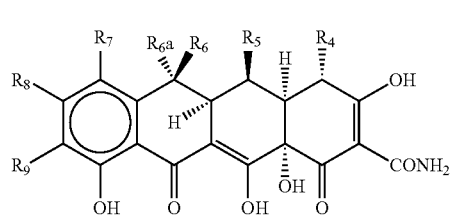

Structure G

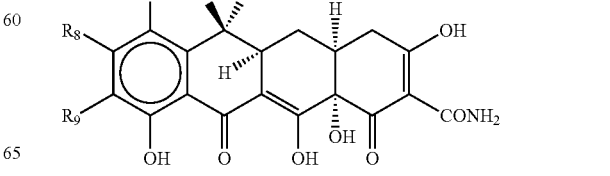

Structure K wherein R7, R8, and R9 taken together in each case, have the following meanings:

| R7 | R8 | R9 |
|---|---|---|
| azido | hydrogen | hydrogen |
| dimethylamino | hydrogen | azido |
| hydrogen | hydrogen | amino |
| hydrogen | hydrogen | azido |
| hydrogen | hydrogen | nitro |
| dimethylamino | hydrogen | amino |
| acylamino | hydrogen | hydrogen |
| hydrogen | hydrogen | acylamino |
| amino | hydrogen | nitro |
| hydrogen | hydrogen | (N,N-dimethyl)glycylamino |
| amino | hydrogen | amino |
| hydrogen | hydrogen | ethoxythiocarbonylthio |
| dimethylamino | hydrogen | acylamino |
| dimethylamino | hydrogen | diazonium |
| dimethylamino | chloro | amino |
| hydrogen | chloro | amino |
| amino | chloro | amino |
| acylamino | chloro | acylamino |
| amino | chloro | hydrogen |
| acylamino | chloro | hydrogen |
| monoalkylamino | chloro | amino |
| nitro | chloro | amino |
| dimethylamino | chloro | acylamino |
| dimethylamino | chloro | dimethylamino |
| dimethylamino | hydrogen | hydrogen |
| hydrogen | hydrogen | dimethylamino | and

General Formula (II)

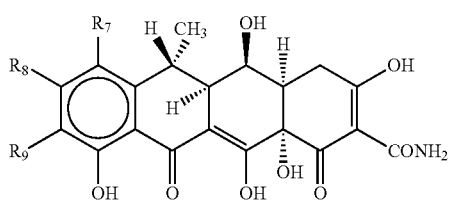

Structure L

Structure M

Structure N

Structure O

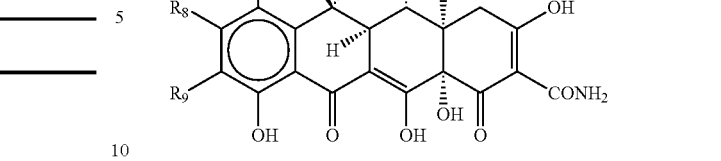

wherein R7, R8, and R9 taken together in each case, have the following meanings:

| R7 | R8 | R9 |
|---|---|---|
| azido | hydrogen | hydrogen |
| dimethylamino | hydrogen | azido |
| hydrogen | hydrogen | amino |
| hydrogen | hydrogen | azido |
| hydrogen | hydrogen | nitro |
| dimethylamino | hydrogen | amino |
| acylamino | hydrogen | hydrogen |
| hydrogen | hydrogen | acylamino |
| amino | hydrogen | nitro |
| hydrogen | hydrogen | (N,N-dimethyl)glycylamino |
| amino | hydrogen | amino |
| hydrogen | hydrogen | ethoxythiocarbonylthio |
| dimethylamino | hydrogen | acylamino |
| hydrogen | hydrogen | diazonium |
| hydrogen | hydrogen | dimethylamino |
| diazonium | hydrogen | hydrogen |
| ethoxythiocarbonylthio | hydrogen | hydrogen |
| dimethylamino | chloro | amino |
| amino | chloro | amino |
| acylamino | chloro | acylamino |
| hydrogen | chloro | amino |
| amino | chloro | hydrogen |
| acylamino | chloro | hydrogen |
| monoalkyl amino | chloro | amino |
| nitro | chloro | amino | and

General Formula (III)

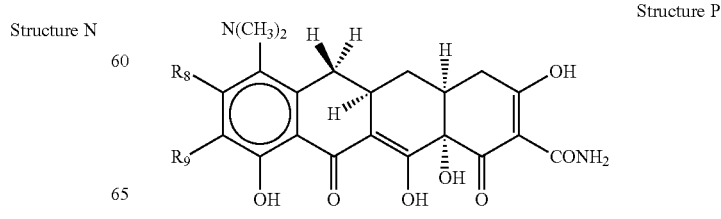

Structure P wherein R8 is hydrogen or halogen and R9 is selected from the group consisting of nitro, (N,N-dimethyl)glycylamino, and ethoxythiocarbonylthio; and General Formula (IV)

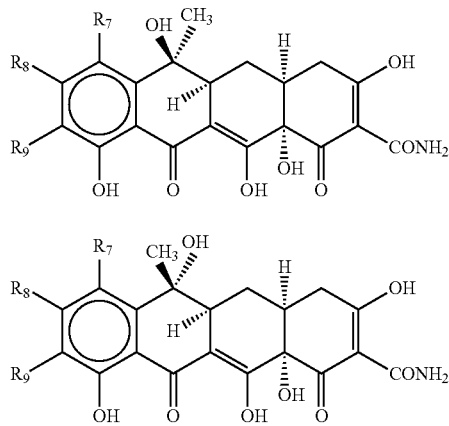

Structure Q

Structure R wherein R7, R8, and R9 taken together in each case, have the following meanings:

| R7 | R8 | R9 |
|---|---|---|
| amino | hydrogen | hydrogen |
| nitro | hydrogen | hydrogen |
| azido | hydrogen | hydrogen |
| dimethylamino | hydrogen | azido |
| hydrogen | hydrogen | amino |
| hydrogen | hydrogen | azido |
| hydrogen | hydrogen | nitro |
| bromo | hydrogen | hydrogen |
| dimethylamino | hydrogen | amino |
| acylamino | hydrogen | hydrogen |
| hydrogen | hydrogen | acylamino |
| amino | hydrogen | nitro |
| hydrogen | hydrogen | (N,N-dimethyl)glycylamino |
| amino | hydrogen | amino |
| diethylamino | hydrogen | hydrogen |
| hydrogen | hydrogen | ethoxythiocarbonylthio |
| dimethylamino | hydrogen | methylamino |
| dimethylamino | hydrogen | acylamino |
| dimethylamino | chloro | amino |
| amino | chloro | amino |
| acylamino | chloro | acylamino |
| hydrogen | chloro | amino |
| amino | chloro | hydrogen |
| acylamino | chloro | hydrogen |
| monoalkylamino | chloro | amino |
| nitro | chloro | amino | and pharmaceutically acceptable and unacceptable salts thereof.

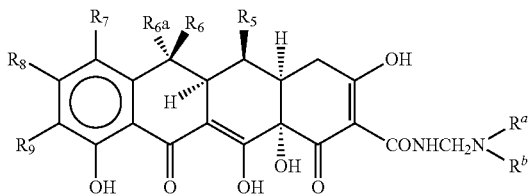

Structure S

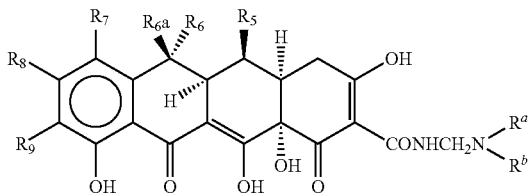

Structure T

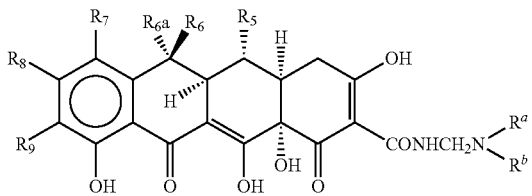

Structure U

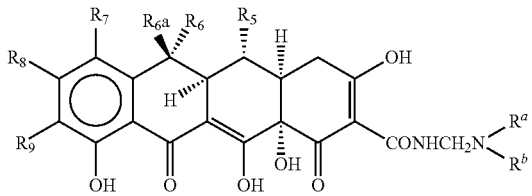

Structure V

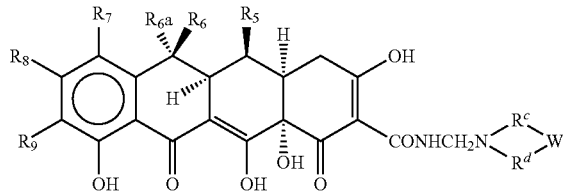

Structure W

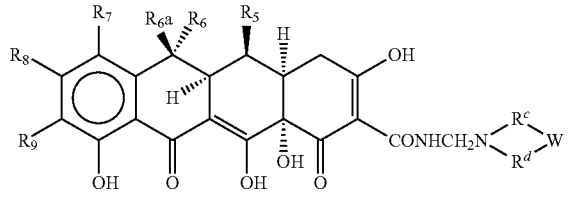

Structure X

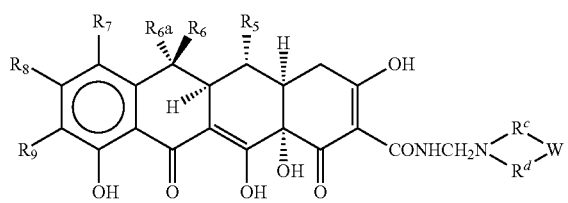

Structure Y

Structure Z

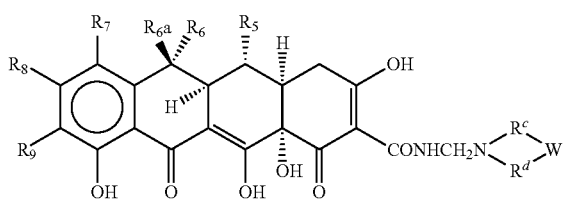

wherein R7 is selected from the group consisting of hydrogen, amino, nitro, mono(lower alkyl)amino, halogen, di(lower alkyl)amino, ethoxythiocarbonylthio, azido, acylamino, diazonium, cyano, and hydroxyl; R6-a is selected from the group consisting of hydrogen and methyl; R6 and R5 are selected from the group consisting of hydrogen and hydroxyl; R8 is selected from the group consisting of hydrogen and halogen; R9 is selected from the group consisting of hydrogen, amino, azido, nitro, acylamino, hydroxy, ethoxythiocarbonylthio, mono(lower alkyl)amino, halogen, diazonium, di(lower alkyl)amino and $RCH(NH_2)CO$; R is hydrogen or lower alkyl; $R^a$ and $R^b$ are selected from the group consisting of hydrogen, methyl, ethyl, n-propyl and 1-methylethyl with the proviso that $R^a$ and $R^b$ cannot both be hydrogen; $R^c$ and $R^d$ are, independently $(CH_2)_nCHR^e$ wherein n is 0 or 1 and $R^e$ is selected from the group consisting of hydrogen, alkyl, hydroxy, lower($C_1$-$C_3$)alkoxy, amino, or nitro; and, W is selected from the group consisting of $(CHR^e)_m$ wherein m is 0-3 and $R^e$ is as above, NH, N($C_1$-$C_3$) straight chained or branched alkyl, O, S and N($C_1$-$C_4$) straight chain or branched alkoxy; and pharmaceutically acceptable and unacceptable salts thereof. In a further embodiment, the following provisos apply: when either R7 and R9 are hydrogen then R8 must be halogen; and when R6-a, R6, R5 and R9 are all hydrogen and R7 is hydrogen, amino, nitro, halogen, dimethylamino or diethylamino, then R8 must be halogen; and when R6-a is methyl, R6 and R9 are both hydrogen, R5 is hydroxyl, and R7 is hydrogen, amino, nitro, halogen or diethylamino, then R8 is halogen; and when R6-a is methyl, R6 is hydroxyl, R5, R7 and R9 are all hydrogen, then R8 must be halogen; and when R6-a, R6 and R5 are all hydrogen, R9 is methylamino and R7 is dimethylamino, then R8 must be halogen; and when R6-a is methyl, R6 is hydrogen, R5 is hydroxyl, R9 is methylamino and R7 is dimethylamino, then R8 must be halogen; and when R6-a is methyl, R6, R5 and R9 are all hydrogen and R7 is cyano, then R8 must be halogen.

Structure K wherein: R7, R8, and R9 taken together in each case, have the following meanings:

| R7 | R8 | R9 |
|---|---|---|
| hydrogen | hydrogen | amino |
| hydrogen | hydrogen | palmitamide | and

Structure L Structure M Structure N Structure O wherein: R7, R8, and R9 taken together in each case, have the following meanings:

| R7 | R8 | R9 |
|---|---|---|
| hydrogen | hydrogen | acetamido |
| hydrogen | hydrogen | dimethylaminoacetamido |
| hydrogen | hydrogen | nitro |
| hydrogen | hydrogen | amino | and

Structure P wherein: R8, and R9 taken together are, respectively, hydrogen and nitro.

Structure K wherein: R7, R8, and R9 taken together are, respectively, hydrogen, hydrogen and dimethylamino.

Structure C Structured Structure E Structure F wherein R7 is selected from the group consisting of an aryl, alkenyl and alkynyl; R6-a is selected from the group consisting of hydrogen and methyl; R6 and R5 are selected from the group consisting of hydrogen and hydroxyl; R8 is selected from the group consisting of hydrogen and halogen; R9 is selected from the group consisting of hydrogen, amino, azido, nitro, acylamino, hydroxy, ethoxythiocarbonylthio, mono(lower alkyl)amino, halogen, diazonium, di(lower alkyl)amino and $RCH(NH_2)CO$; and pharmaceutically acceptable and unacceptable salts thereof; or Structure C Structured Structure E Structure F wherein: R7 is selected from the group consisting of hydrogen, amino, nitro, mono(lower alkyl)amino, halogen, di(lower alkyl)amino, ethoxythiocarbonylthio, azido, acylamino, diazonium, cyano, and hydroxyl; R6-a is selected from the group consisting of hydrogen and methyl; R6 and R5 are selected from the group consisting of hydrogen and hydroxyl; R8 is selected from the group consisting of hydrogen and halogen; R9 is selected from the group consisting of an aryl, alkenyl and alkynyl; and pharmaceutically acceptable and unacceptable salts thereof;

or

Structure C Structured Structure E Structure F wherein: R7 and R9 are selected from the group consisting of an aryl, alkene, alkyne, or mixtures thereof; R6-a is selected from the group consisting of hydrogen and methyl; R6 and R5 are selected from the group consisting of hydrogen and hydroxyl; R8 is selected from the group consisting of hydrogen and halogen; and pharmaceutically acceptable and unacceptable salts thereof.

Structure G Structure H Structure I Structure J wherein R7 is selected from the group consisting of an aryl, alkenyl and alkynyl; R6-a is selected from the group consisting of hydrogen and methyl; R6 and R5 are selected from the group consisting of hydrogen and hydroxyl; R4 is selected from the group consisting of NOH, N—NH-A, and NH-A, where A is a lower alkyl group; R8 is selected from the group consisting of hydrogen and halogen; R9 is selected from the group consisting of hydrogen, amino, azido, nitro, acylamino, hydroxy, ethoxythiocarbonylthio, mono(lower alkyl)amino, halogen, di(lower alkyl)amino and RCH(NH$_2$)CO; and pharmaceutically acceptable and unacceptable salts thereof;
or Structure G Structure H Structure I Structure J wherein R7 is selected from the group consisting of hydrogen, amino, nitro, mono(lower alkyl)amino, halogen, di(lower alkyl)amino, ethoxythiocarbonylthio, azido, acylamino, diazonium, cyano, and hydroxyl; R6-a is selected from the group consisting of hydrogen and methyl; R6 and R5 are selected from the group consisting of hydrogen and hydroxyl; R4 is selected from the group consisting of NOH, N—NH-A, and NH-A, where A is a lower alkyl group; R8 is selected from the group consisting of hydrogen and halogen; R9 is selected from the group consisting of an aryl, alkenyl and alkynyl; and pharmaceutically acceptable and unacceptable salts thereof;
or Structure G Structure H Structure I Structure J wherein: R7 and R9 are selected from the group consisting of an aryl, alkenyl, alkynyl; or mixtures thereof; R6-a is selected from the group consisting of hydrogen and methyl; R6 and R5 are selected from the group consisting of hydrogen and hydroxyl; R4 is selected from the group consisting of NOH, N—NH-A, and NH-A, where A is a lower alkyl group; and R8 is selected from the group consisting of hydrogen and halogen; and pharmaceutically acceptable and unacceptable salts thereof.

Structure K wherein R7 is selected from the group consisting of an aryl, alkenyl and alkynyl; R8 is selected from the group consisting of hydrogen and halogen; R9 is selected from the group consisting of hydrogen, amino, azido, nitro, acylamino, hydroxy, ethoxythiocarbonylthio, mono(lower alkyl)amino, halogen, di(lower alkyl)amino and RCH(NH$_2$)CO; and pharmaceutically acceptable and unacceptable salts thereof;
or Structure K wherein: R7 is selected from the group consisting of hydrogen, amino, nitro, mono(lower alkyl)amino, halogen, di(lower alkyl)amino, ethoxythiocarbonylthio, azido, acylamino, diazonium, cyano, and hydroxyl; R8 is selected from the group consisting of hydrogen and halogen; R9 is selected from the group consisting of an aryl, alkenyl and alkynyl; and pharmaceutically acceptable and unacceptable salts thereof;
or Structure K wherein: R7 and R9 are selected from the group consisting of an aryl, alkenyl, alkynyl and mixtures thereof; and R8 is selected from the group consisting of hydrogen and halogen; and pharmaceutically acceptable and unacceptable salts thereof;
and Structure L Structure M Structure N Structure O wherein: R7 is selected from the group consisting of an aryl, alkenyl and alkynyl; R8 is selected from the group consisting of hydrogen and halogen; and pharmaceutically acceptable and unacceptable salts thereof;
or Structure L Structure M Structure N Structure O wherein R7 is selected from the group consisting of hydrogen, amino, nitro, mono(lower alkyl)amino, halogen, di(lower alkyl)amino, ethoxythiocarbonylthio, azido, acylamino, diazonium, cyano, and hydroxyl; R8 is selected from the group consisting of hydrogen and halogen; R9 is selected from the group consisting of an aryl, alkenyl and alkynyl; and pharmaceutically acceptable and unacceptable salts thereof;
or Structure L Structure M Structure N Structure O wherein R7 is and R9 are selected from the group consisting of an aryl, alkenyl, alkynyl and mixtures thereof; R8 is selected from the group consisting of hydrogen and halogen; R9 is selected from the group consisting of hydrogen, amino, azido, nitro, acylamino, hydroxy, ethoxythiocarbonylthio, mono(lower alkyl)amino, halogen, di(lower alkyl)amino and RCH(NH$_2$)CO; and pharmaceutically acceptable and unacceptable salts thereof;
and Structure P wherein R9 is selected from the group consisting of an aryl, alkenyl and alkynyl; and R8 is selected from the group consisting of hydrogen and halogen; and pharmaceutically acceptable and unacceptable salts thereof;
and Structure Q Structure R wherein R7 is selected from the group consisting of an aryl, alkenyl and alkynyl; R8 is selected from the group consisting of hydrogen and halogen; R9 is selected from the group consisting of hydrogen, amino, azido, nitro, acylamino, hydroxy, ethoxythiocarbonylthio, mono(lower alkyl)amino, halogen, di(lower alkyl)amino and RCH(NH$_2$)CO; and pharmaceutically acceptable and unacceptable salts thereof;
or Structure Q Structure R wherein R7 is selected from the group consisting of hydrogen, amino, nitro, mono(lower alkyl)amino, halogen, di(lower alkyl)amino, ethoxythiocarbonylthio, azido, acylamino, diazonium, cyano, and hydroxyl; R8 is selected from the group consisting of hydrogen and halogen; R9 is selected from the group consisting of an aryl, alkenyl and alkynyl; and pharmaceutically acceptable and unacceptable salts thereof;
or Structure Q Structure R wherein R7 and R9 are selected from the group consisting of an aryl, alkenyl, alkynyl; and mixtures thereof; R8 is selected from the group consisting of hydrogen and halogen; and pharmaceutically acceptable and unacceptable salts thereof.

Structures S-Z wherein R7 is selected from the group consisting of an aryl, alkenyl and alkynyl; R6-a is selected from the group consisting of hydrogen and methyl; R6 and R5 are selected from the group consisting of hydrogen and hydroxyl; R8 is selected from the group consisting of hydrogen and halogen; R9 is selected from the group consisting of hydrogen, amino, azido, nitro, acylamino, hydroxy, ethoxythiocarbonylthio, mono(lower alkyl)amino, halogen, diazonium, di(lower alkyl)amino and $RCH(NH_2)CO$; $R^a$ and $R^b$ are selected from the group consisting of hydrogen, methyl, ethyl, n-propyl and 1-methylethyl with the proviso that $R^a$ and $R^b$ cannot both be hydrogen; $R^c$ and $R^d$ are, independently, $(CH_2)_nCHR^e$ wherein n is 0 or 1 and $R^e$ is selected from the group consisting of hydrogen, alkyl, hydroxy, lower($C_1$-$C_3$)alkoxy, amino, or nitro; and, W is selected from the group consisting of $(CHR^e)_m$ wherein m is 0-3 and said $R^e$ is as above, NH, N($C_1$-$C_3$) straight chained or branched alkyl, O, S and N($C_1$-$C_4$) straight chain or branched alkoxy; and pharmaceutically acceptable and unacceptable salts thereof;

or

Structures S-Z wherein R7 is selected from the group consisting of hydrogen, amino, nitro, mono(lower alkyl)amino, halogen, di(lower alkyl)amino, ethoxythiocarbonylthio, azido, acylamino, diazonium, cyano, and hydroxyl; R6-a is selected from the group consisting of hydrogen and methyl; R6 and R5 are selected from the group consisting of hydrogen and hydroxyl; R8 is selected from the group consisting of hydrogen and halogen; R9 is selected from the group consisting of an aryl, alkenyl and alkynyl; $R^a$ and $R^b$ are selected from the group consisting of hydrogen, methyl, ethyl, n-propyl and 1-methylethyl with the proviso that $R^a$ and $R^b$ cannot both be hydrogen; $R^c$ and $R^d$ are, independently, $(CH_2)_nCHR^e$ wherein n is 0 or 1 and $R^e$ is selected from the group consisting of hydrogen, alkyl, hydroxy, lower($C_1$-$C_3$)alkoxy, amino, or nitro; and, W is selected from the group consisting of $(CHR^e)_m$ wherein m is 0-3 and said $R^e$ is as above, NH, N($C_1$-$C_3$) straight chained or branched alkyl, O, S and N($C_1$-$C_4$) straight chain or branched alkoxy; and pharmaceutically acceptable and unacceptable salts thereof;

or

Structures S-Z wherein: R7 and R9 are selected from the group consisting of an aryl, alkenyl, alkynyl and mixtures thereof; R6-a is selected from the group consisting of hydrogen and methyl; R6 and R5 are selected from the group consisting of hydrogen and hydroxyl; R8 is selected from the group consisting of hydrogen and halogen; $R^a$ and $R^b$ are selected from the group consisting of hydrogen, methyl, ethyl, n-propyl and 1-methylethyl with the proviso that $R^a$ and $R^b$ cannot both be hydrogen; $R^c$ and $R^d$ are, independently, $(CH_2)_nCHR^e$ wherein n is 0 or 1 and $R^e$ is selected from the group consisting of hydrogen, alkyl, hydroxy, lower($C_1$-$C_3$)alkoxy, amino, or nitro; and W is selected from the group consisting of $(CHR^e)_m$ wherein m is 0-3 and said $R^e$ is as above, NH, N($C_1$-$C_3$) straight chained or branched alkyl, O, S and N($C_1$-$C_4$) straight chain or branched alkoxy; and pharmaceutically acceptable and unacceptable salts thereof.

What is claimed is:

1. A method for treating acne in a human in need thereof, the method comprising
    administering orally to said human doxycycline, or a pharmaceutically acceptable salt thereof,
    in an amount that
    (i) is effective to treat acne;
    (ii) is 10-80% of a 50 mg dose of doxycycline per day; and
    (iii) results in no reduction of skin microflora during a six-month treatment, without administering a bisphosphonate compound.

2. The method according to claim 1, wherein said doxycycline is doxycycline monohydrate.

3. The method according to claim 2, wherein said doxycycline monohydrate is administered in an amount of 40 milligrams.

4. The method according to claim 3, wherein said doxycycline monohydrate is administered by sustained release.

5. A method according to claim 4, wherein said doxycycline monohydrate is administered once a day.

6. The method according to claim 2, wherein said doxycycline monohydrate is administered in a dose of 20 mg twice a day.

7. The method according to claim 1, wherein said doxycycline, or a pharmaceutically acceptable salt thereof, is administered in an amount which provides a serum concentration in the range of about 0.1 to about 0.8 µg/ml.

8. A method for treating acne in a human in need thereof, the method comprising
    administering orally to said human doxycycline, or a pharmaceutically acceptable salt thereof,
    in an amount that
    (i) is effective to treat acne;
    (ii) is 40-80% of a 50 mg dose of doxycycline per day; and
    (iii) results in no reduction of skin microflora during a six-month treatment, without administering a bisphosphonate compound.

9. The method according to claim 8, wherein said doxycycline is doxycycline monohydrate.

10. The method according to claim 9, wherein said doxycycline monohydrate is administered in an amount of 40 milligrams.

11. The method according to claim 10, wherein said doxycycline monohydrate is administered by sustained release.

12. A method according to claim 11, wherein said doxycycline monohydrate is administered once a day.

13. The method according to claim 9, wherein said doxycycline monohydrate is administered in a dose of 20 mg twice a day.

14. The method according to claim 8, wherein said doxycycline, or a pharmaceutically acceptable salt thereof, is administered in an amount which provides a serum concentration in the range of about 0.1 to about 0.8 µg/ml.

15. A method for treating acne in a human in need thereof, the method comprising
    administering orally to said human doxycycline, or a pharmaceutically acceptable salt thereof, in an amount of 40 mg per day, wherein the amount results in no reduction of skin microflora during a six-month treatment, without administering a bisphosphonate compound.

16. The method according to claim 15, wherein said doxycycline is doxycycline monohydrate.

17. The method according to claim 16, wherein said doxycycline monohydrate is administered by sustained release.

18. A method according to claim 17, wherein said doxycycline monohydrate is administered once a day.

19. The method according to claim 16, wherein said doxycycline monohydrate is administered in a dose of 20 mg twice a day.

20. The method according to claim 15, wherein said doxycycline, or a pharmaceutically acceptable salt thereof, is administered in an amount which provides a serum concentration in the range of about 0.1 to about 0.8 μg/ml.

* * * * *

UNITED STATES PATENT AND TRADEMARK OFFICE
CERTIFICATE OF CORRECTION

PATENT NO. : 8,658,189 B2
APPLICATION NO. : 13/838559
DATED : February 25, 2014
INVENTOR(S) : Robert A. Ashley It is certified that error appears in the above-identified patent and that said Letters Patent is hereby corrected as shown below:

IN THE SPECIFICATION:

Column 10, line 13:
 Now reads: "with stifling."
 Should read: -- with stirring. --

Column 11, line 37:
 Now reads: "with stifling."
 Should read: -- with stirring. --

Signed and Sealed this
Nineteenth Day of August, 2014

Michelle K. Lee
*Deputy Director of the United States Patent and Trademark Office*